United States Patent
Naruse et al.

[11] Patent Number: 5,514,793
[45] Date of Patent: May 7, 1996

[54] 1,3,6-TRIALKYLHEXAHYDRO-1,3,6-TRIAZOCINE-2-ON AND PREPARATION PROCESS THEREOF

[75] Inventors: Hiroshi Naruse; Hideki Mizuta; Shinichi Umeda; Teruyuki Nagata, all of Fukuoka, Japan

[73] Assignee: Mitsui Toatsu Chemicals, Inc., Tokyo, Japan

[21] Appl. No.: 389,934

[22] Filed: Feb. 17, 1995

[30] Foreign Application Priority Data

Mar. 1, 1994 [JP] Japan .................................. 6-031174

[51] Int. Cl.$^6$ ................................................ C07D 255/02
[52] U.S. Cl. .................................. 540/460; 252/364
[58] Field of Search ............................................. 540/460

[56] References Cited

FOREIGN PATENT DOCUMENTS

| 1184766 | 1/1965 | Germany | 540/460 |
|---------|--------|---------|---------|
| 2952125 | 6/1981 | Germany | 540/460 |

OTHER PUBLICATIONS

Synthesis, No. 8, 1975, pp. 483–495, "Synthesis of Heterocycles . . . ", Anderson et al.

*Primary Examiner*—Robert T. Bond
*Attorney, Agent, or Firm*—Burns, Doane, Swecker & Mathis

[57] ABSTRACT

The present invention relates to 1,3,6-Trialkylhexahydro-1,3,6-triazocine-2-on represented by the formula (1):

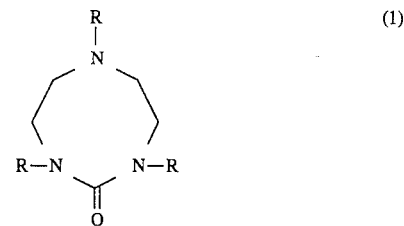

wherein R is a $C_1$~$C_8$ alkyl group and a preparation process of the compound comprising reacting N,N',N"-trialkyldiethylenetriamine represented by the formula (2):

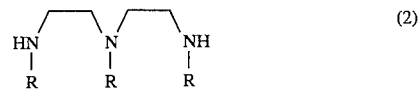

wherein R is a $C_1$~$C_8$ alkyl group, with urea, phosgene or carbon dioxide.

6 Claims, 3 Drawing Sheets

1,3,6-TRIALKYLHEXAHYDRO-1,3,6-TRIAZOCINE-2-ON AND PREPARATION PROCESS THEREOF

BACKGROUND OF THE INVENTION

1. Field of the Invention

The present invention relates to a novel aprotic polar compound 1,3,6-trialkylhexahydro -1,3,6-triazocine-2-on represented by the formula (1):

$$\begin{array}{c} R \\ | \\ N \\ \diagup \diagdown \\ \diagdown \diagup \\ R-N \quad N-R \\ \diagdown C \diagup \\ \| \\ O \end{array} \quad (1)$$

wherein R is a $C_1$–$C_8$ alkyl group, and a preparation process of the compound. The compounds are a useful substance as a solvent for synthesis and polymerization reactions and an intermediate for cleaning agents and surface active agents.

2. Description of the Related Art 1,3-Dimethyl-2-imidazolidinone and N-methyl-2-pyrrolidone have been conventionally known as aprotic polar compounds.

These compounds are useful as a solvent and particularly excellent as a solvent for polyamide, polyvinyl chloride, polyvinyl alcohol, polystyrene, polyurethane, phenolic resin and other high polymers. Further, these compounds can also be used as a solvent for many organic reactions. However, these conventionally known aprotic polar compounds have many problems. For example, 1,3-dimethyl-2-imidazolidinone has poor resistance to oxidation at high temperatures, and N-methyl-2-pyrrolidone leads to chromosome aberration.

SUMMARY OF THE INVENTION

An object of the invention is to provide novel aprotic polar compounds having an excellent solvent effect.

As a result of an intensive investigation in order to develop a novel aprotic polar solvent, the present inventors have succeeded in the preparation of 1,3,6-trialkylhexahydro-1,3,6-triazocine-2-on which has a cyclic urea structure similar to 1,3-dimethyl-2-imidazolidinone and can expect high polarity, and have found that the novel compounds exert an excellent solvent effect as an aprotic polar substance. Thus, the present invention has been completed.

That is, one aspect of the present invention is 1,3,6-trialkylhexahydro-1,3,6-triazocine-2-on represented by the formula (1):

$$\begin{array}{c} R \\ | \\ N \\ \diagup \diagdown \\ \diagdown \diagup \\ R-N \quad N-R \\ \diagdown C \diagup \\ \| \\ O \end{array} \quad (1)$$

wherein R is a $C_1$–$C_8$ alkyl group.

Another aspect of the present invention is a process for preparing the 1,3,6-trialkylhexahydro-1,3,6-triazocine-2-on comprising reacting N,N',N''-trialkyldiethylenetriamine represented by the formula (2):

$$\begin{array}{c} \diagup \diagdown \diagup \diagdown \\ HN \quad N \quad NH \\ | \quad | \quad | \\ R \quad R \quad R \end{array} \quad (2)$$

wherein R is a $C_1$–$C_8$ alkyl group, with urea, phosgene or carbon dioxide.

1,3,6-Trialkylhexahydro-1,3,6-triazocine-2-on of the present invention exhibits a solvent effect which compares advantageously with conventional aprotic polar solvents.

Consequently, the present invention can provide a novel aprotic substance having an excellent solvent effect and thus has a great significance.

BRIEF DESCRIPTION OF THE DRAWINGS

FIG. 1 shows an IR spectrum of 1,3,6-trimethylhexahydro-1,3,6-triazocine-2-on.

FIG. 2 shows an IR spectrum of 1,3,6-tri-n-propylhexahydro-1,3,6-triazocine-2-on.

FIG. 3 shows an IR spectrum of 1,3,6-tri-n-butylhexahydro-1,3,6-triazocine-2-on.

DETAILED DESCRIPTION OF THE INVENTION

Figure 1:
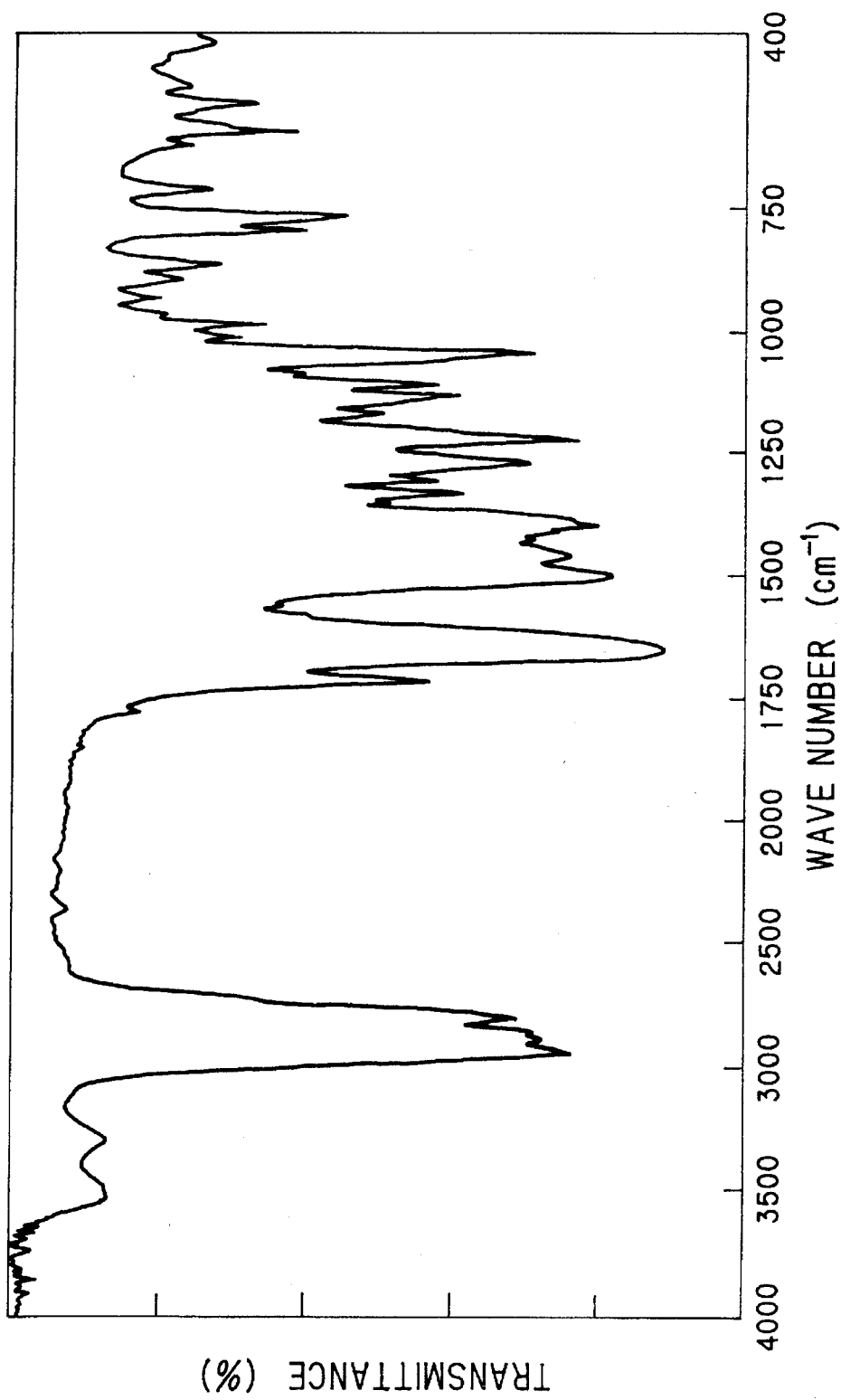

In-the formula (1), R is an alkyl group having 1~8 carbon atoms. Exemplary alkyl groups include methyl, ethyl, n-propyl, i-propyl, n-butyl, i-butyl, s-butyl, t-butyl, n-pentyl, i-pentyl, 2-pentyl, 3-pentyl, neopentyl, n-hexyl, i-hexyl, n-heptyl, i-heptyl, n-octyl and i-octyl groups.

N,N',N''-trialkyldiethylenetriamine which can be used in the process of the invention can be prepared by the following reaction:

$$X \diagup \diagdown X + R\,NH_2 \longrightarrow HN \diagup \diagdown N \diagup \diagdown NH$$
$$\qquad\qquad\qquad\qquad\quad | \quad | \quad |$$
$$\qquad\qquad\qquad\qquad\quad R \quad R \quad R$$

wherein x is a halogen atom, and R is an $C_1$–$C_8$ alkyl group.

The triamine can also be prepared, when needed, by reacting N,N'-dialkylethylenediamine with 1,2-dihalogenoethane in the coexistence of corresponding alkylamine. N,N',N''-trialkyldiethylenetriamine thus obtained reacts with urea, phosgene or carbon dioxide and undergoes a cyclization to give 1,3,6-trialkylhexahydro-1,3,6-triazocine-2-on.

In the preferred preparation process of the intermediate N,N',N''-trialkyldiethylenetriamine, the molar ratio of alkyl amine to 1,2-dihalogenoethane is preferably 4–6. When the molar ratio of alkylamine is high, an intermediate by-product N,N'-dialkylethylenediamine is liable to increase.

No particular limitation is imposed upon the reaction temperature for aminating 1,2-dihalogenoethane as long as the temperature is in the range of giving a suitable reaction rate. The temperature range is preferably 80°~150° C.

The amination reaction is carried out under increased pressure depending upon the reaction temperature. In practice, when amines having a boiling point higher than that of n-butylamine (boiling point : 78° C.) are used, the reaction can progress at atmospheric pressure. However, when amines having a boiling point lower than that of n-butylamine, the reaction must be carried out under increased pressure.

Conventionally known solvents can be used for the amination reaction with no difficulty of any kind. The amination reaction, however, is usually carried out without solvent, that is, in the presence of alkylamine and 1,2-dihalogenoethane only.

N,N',N''-trialkyldiethylenetriamine thus formed can be separated by neutralizing the reaction mixture of amination with sodium hydroxide or other suitable base and distilling off unreacted alkyl amine. Pure product can be obtained by further distillating the residue.

In the first step of the process of the invention, a urea intermediate is initially formed by the reaction of N,N',N''-trialkyldiethylenetriamine with urea. The reaction temperature is preferably in the range of 100°~155° C., more preferably 120°~145° C. The reaction temperature higher than 155° C. leads to decomposition of urea. On the other hand, when the reaction temperature is lower than 100° C., the reaction rate becomes unfavorably slow. The urea intermediate formation in the initial reaction progresses quantitatively and the end point of the reaction can be detected by determining gaseous ammonia released with progress of the reaction.

The decomposition reaction of the urea intermediate is carried out by successively raising the reaction temperature to 180° C. or more, preferably 200°~260° C., more preferably 210°~240° C. Thus, 1,3,6-trialkylhexahydro- 1,3,6-triazocine-2-on can be obtained in high yield. When the temperature is less than 180° C., rate of the decomposition reaction becomes unfavorably slow. On the other hand, the temperature around 300° C. leads to problems on the heating means.

In the process of the invention, N,N',N''-trimethyldiethylenetriamine is used in an amount of 0.8~2.5 mole, preferably 1.0~2.0 mole, more preferably 1.2~1.7 mole for 1 mole of urea. When the amount of N,N',N''-trimethyldiethylenetriamine is less than 0.8 mole, formation of the by-products increase. On the other hand, the amount more than 2.5 mole unfavorably leads to disadvantages in industry, for example, decrease in volume efficiency.

Solvents which can be used for the reaction in the process of the invention include, for example, ethanol, methyl isobutyl ketone, N-methyl-2-pyrrolidone, 1,3-dimethyl-2-imidazolidinone, diethylene glycol dimethyl ether and triethylene glycol dimethyl ether. However, the process of the invention can be also be carried out without solvent. That is, even a reaction proceeded in the presence of N,N',N''-trialkyldiethylenetriamine and urea only can provide 1,3,6-trialkylhexahydro-1,3,6-traizocine-2-on in the yield equivalent to, or higher than the yield obtained in the presence of the solvent. Consequently, the reaction is desirably carried out without solvent in view of avoiding complex procedures such as removal of the solvent by distillation. Further, the reaction can be carried out at the atmospheric pressure when a high boiling point solvent is used. However, when a low boiling point solvent is used, the reaction is required to carry out under increased pressure, which is disadvantageous in industry in view of production facilities. However, N,N',N''-trimethyldiethylenetriamine has the lowest boiling point in N,N',N''-trialkyldiethylenetriamine and still has a boiling point of 201° C. Consequently, increased pressure is not required and thus reaction without solvent is preferred.

1,3,6-trialkylhexahydro-1,3,6-triazocine-2-on thus formed can be purified by distillation. Unreacted N,N',N''-trialkyldiethylenetriamine is recovered as a fore-running distillate of 1,3,6-trialkylhexahydro-1,3,6-triazoine-2-on and can be reused.

The present invention will hereinafter be illustrated in detail by way of examples and reference examples.

EXAMPLE 1

To a 5.0 liter autoclave equipped with a thermometer and stirrer, 1286.5 g (13 mole) of 1,2-dichloroethane and 2018.9 g (65 mole) of methylamine were charged. The mixture was heated to 100° C. with stirring and amination reaction was continued for 2 hours while maintaining the same temperature.

The reaction mixture was successively cooled to the room temperature and excess methylamine was recovered by releasing pressure of the reaction vessel. The reaction mass in this stage was analyzed by gas chromatography. 1,2-Dichloroethane was completely converted. Successively, 1072.2 g of 97% flake sodium hydroxide was charged in order to neutralize the reaction mass and then unreacted methylamine was recovered by distillation. Sodium chloride precipitated in the reaction mass after distillation was filtered off and the filtrate was distilled to separate 229.4 g of N,N',N''-trimethyldiethylenetriamine.

To a 0.5 liter flask equipped with a reflux condenser, thermometer and stirrer, 217.9 g (1.5 moles) of N,N',N''-trimethyldiethylenetriamine and 60.1 g (1.0 mole) of urea were charged and reacted at 125°~140° C. with stirring for 4 hours.

The temperature was successively raised to 215°~225° C. and the decomposition reaction of urea intermediate was carried out for 8 hours at this temperature. After finishing the reaction, 1,3,6-trimethylhexahydro-1,3,6-triazocine-2-on was determined by gas chromatography. The yield was 80.3% based on urea. The reaction mixture was distilled to recover 63.2 g of unreacted N,N',N''-trimethyldiethylenetriamine in the first step and then 127.1 g of 1,3,6-trimethylhexahydro-1,3,6-triazocine-2-on was obtained. The product had a boiling point of 258° C. and purity of 99.0%.

The structure of 1,3,6-trimethylhexahydro-1,3,6-triazocine-2-on was identified by $^1$H NMR, $^{13}$C NMR, IR and MS m/z: 171 (M$^+$).

○$^1$H NMR, δ(CDCl$_3$, 400 MHz) 2.42(s,3H, ④), 2.66(m, 4H, ③), 2.78(s,6H, ①), 3.33(m,4H, ②),

○$^{13}$C NMR, δ(CDCl$_3$, 100 MHz) 36.8(q, ①), 46.6(q, ④), 53.8(t, ②), 54.7(t, ③), 163.7(s,C=0, ⑤), wherein (①)~(④) indicate positions on the following formula;

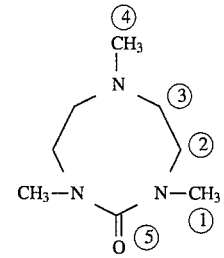

FIG. 1 illustrates IR charts 1,3,6-trimethylhexahydro-1,3,6-triazocine-2-on.

EXAMPLE 2

The reaction and analyses were carried out by the same procedures as described in Example 1 except that n-propylamine was used in place of methylamine. As a result, the yield of 1,3,6-tri-n-propylhexahydro-1,3,6-triazocine-2-on was 66.5% based on urea. The structure of 1,3,6-tri-n-propylhexahydro-1,3,6-triazocine-2-on was identified by $^1$H NMR, $^{13}$C NMR, IR and MS m/z: 297 (M$^+$).

○$^1$H NMR, δ(CDCl$_3$, 400 MHz) 0.89 (t,9H, ① and ⑧), 1.50(m,2H, ⑦), 1.56(m,4H, ②), 2.47(t,2H, ⑥), 2.70(m,4H, ④), 3.09(t,4H, ③), 3.35(t,4H, ⑤), ○ $^{13}$C NMR, δ( CDCl$_3$, 100 MHz) 11.5(q, ①), 11.7(q, ⑧), 20.4(t, ⑦), 21.0(t, ②), 51.5(t, ③), 51.8(t, ⑤), 53.3(t, ④), 60.3(t, ⑥), 163.5(s, C=0, ⑨), wherein (①)~(⑧) indicate positions on the following formula;

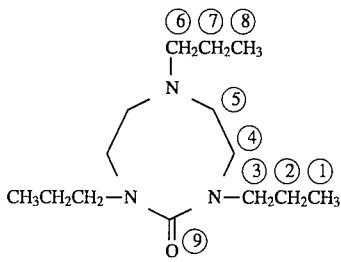

Figure 2:
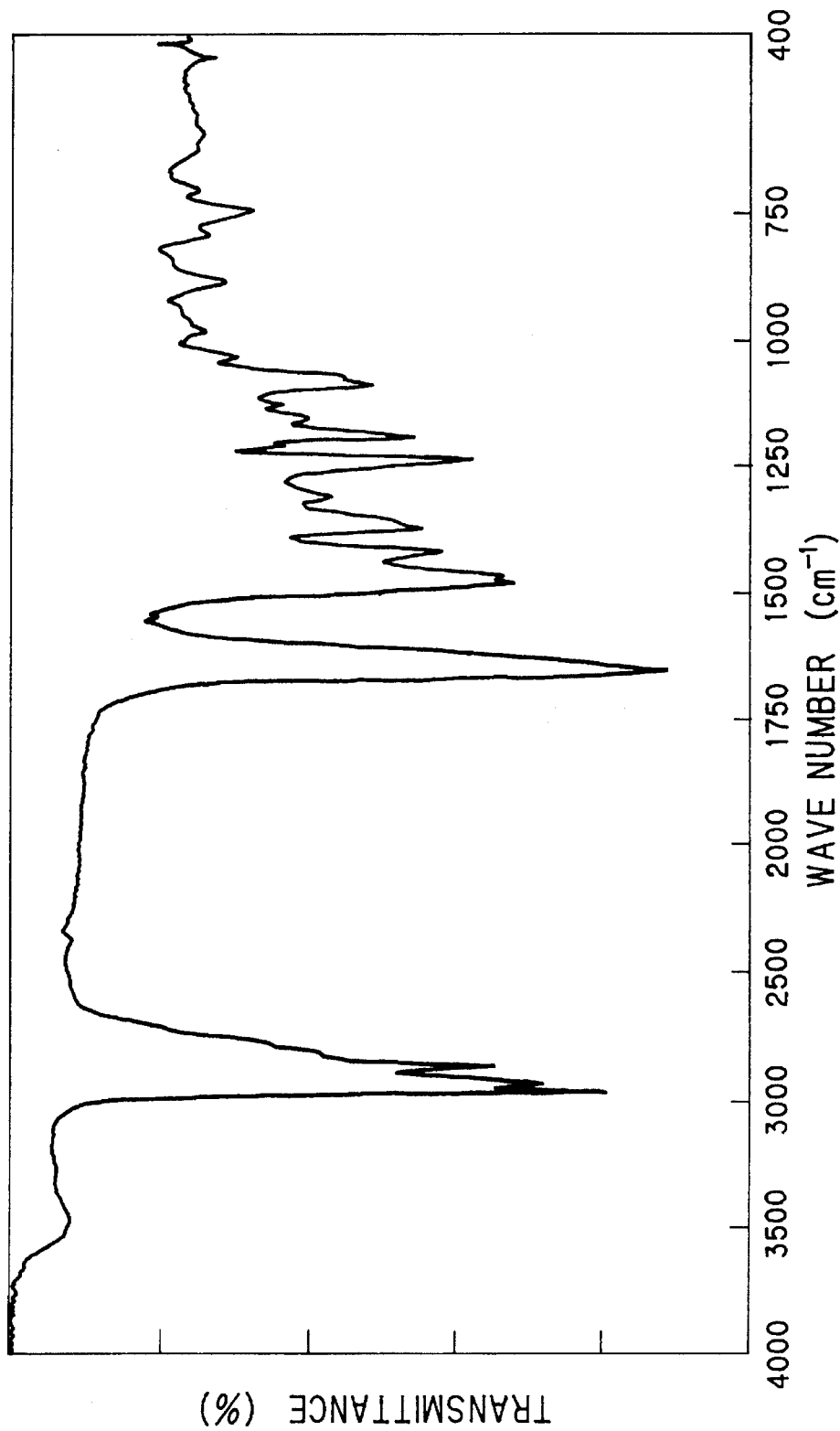

FIG. 2 illustrates IR charts of 1,3,6-tri-n-propylhexahydro-1,3,6-triazocine-2-on.

EXAMPLE 3

The reaction and analyses were carried out by the same procedures as described in Example 1 except that n-butylamine was used in place of methylamine and the synthesis of N,N',N,"-tri-n-butyldiethylenetriamine was carried out at the atmospheric pressure. As a result, the yield of 1,3,6-tri-n-butylhexahydro-1,3,6-triazocine-2-on was 51.5 % based on urea. The structure of 1,3,6-tri-n-butylhexahydro-1,3,6-triazocine-2-on was identified by $^1$H NMR, $^{13}$C NMR, IR and MS m/z: 256(M$^+$).

○ $^1$H NMR, δ(CDCl$_3$, 400 MHz) 0.90(t,3H, ⑩), 0.91(t, 6H, ①), 1.30(m,6H, ② and ⑨) 1.42(m,2H, ⑧), 1.52(m,4H, ③), 2.48(t,2H, ⑦), 2.67(m,4H, ⑤), 3.11(t,4H, ④), 3.34(m,4H, ⑥), ○ $^{13}$C NMR, δ(CDCl$_3$, 100 MHz) 13.8(q, ①), 13.9(q, ⑩), 20.1(t, ②), 20.3(t, ⑨), 29.4(t, ⑧), 29.6(t, ③), 49.5(t, ④), 51.8(t, ⑥), 53.2(t, ⑤), 58.0(t, ⑦), 163.4(s, C=0, ⑪)

wherein (①)~(⑩) indicate positions on the following formula;

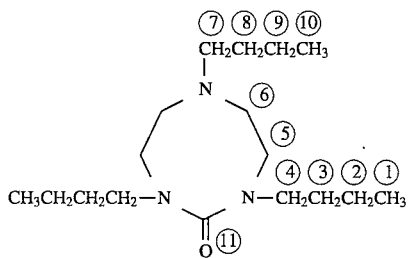

Figure 3:
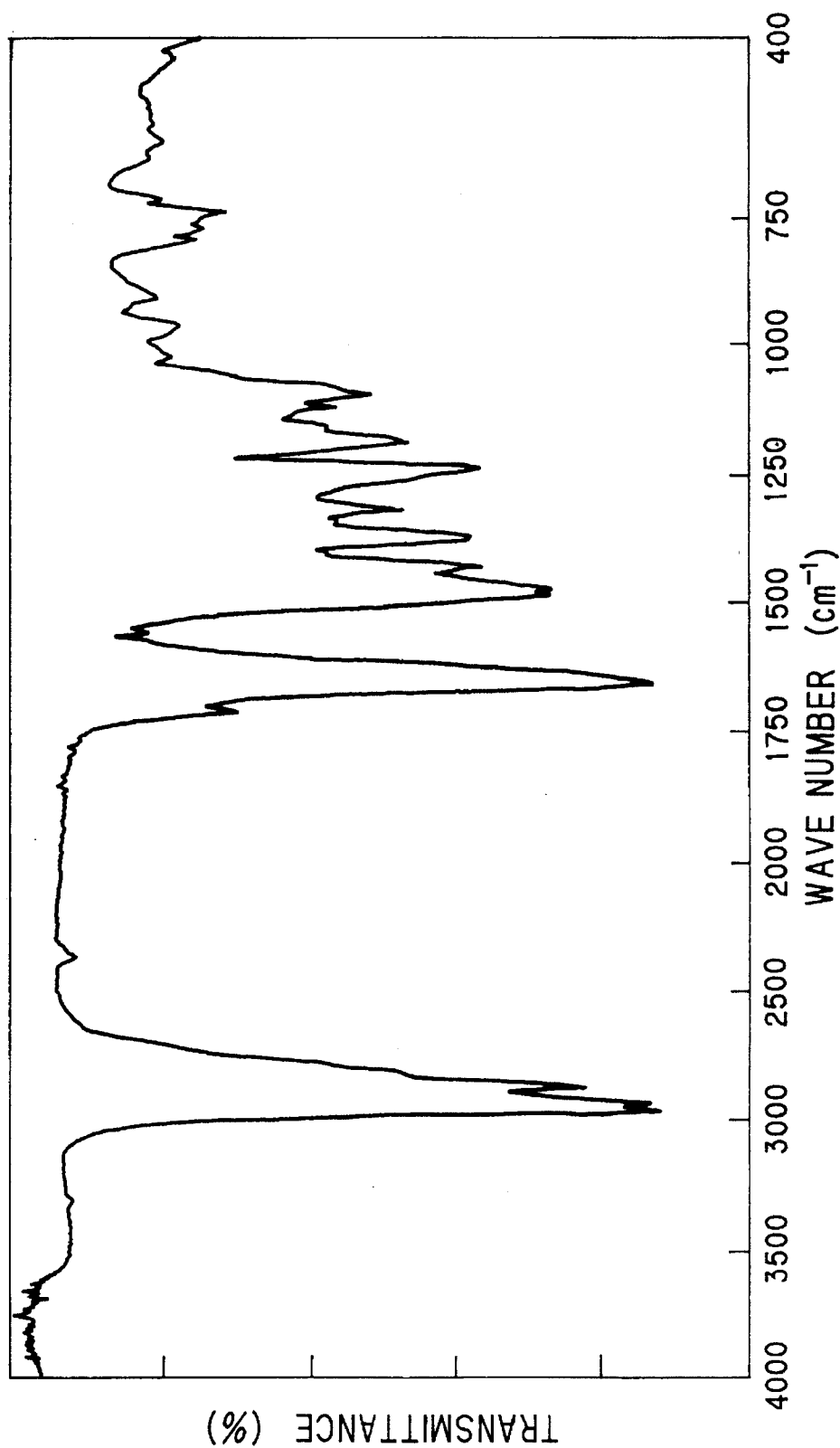

FIG. 3 illustrates IR charts of 1,3,6-tri-n-butylhexahydro-1,3,6-triazocine-2-on.

Reference Example 1

To a 0.3 liter reaction vessel equipped with a stirrer and thermometer, 25.1 g (0.1 mole) of 4,4'-dichlorobenzophenone, 24.0 g (0.22 mole) of m-aminophenol, 12.9 g (0.22 mole) of 96% potassium hydroxide and 150 g of 1,3,6-trimethylhexahydro-1,3,6-triazocine-2-on obtained in Example 1 as a solvent were charged and reacted at 150°~160° C. for 8 hours.

After finishing the reaction, the reaction mass was cooled to the room temperature and the inorganic salt formed was filtered. The solvent was distilled off from the filtrate under reduced pressure. The residual mass was mixed with 20.8 g of 35% hydrochloric acid and 100 g of water and dissolved by heating. Successively 11.7 g of sodium chloride was added to the solution thus obtained and cooled to 20°~25° C. with stirring to precipitate hydrochloride salt. The hydrochloride was filtered, recrystallized from a 10% aqueous sodium chloride solution and neutralized with an aqueous ammonia solution in a 50% aqueous isopropyl alcohol solution. Precipitated crystals were filtered, washed with water and dried to obtain 25.6 g (88.3% yield) of 4,4'-bis(3-aminophenoxy)benzophenone in the form of white crystals. The purity was 99.5% by high performance liquid chromatography.

Reference Example 2

The same procedures as described in Reference Example 1 were carried out except that the reaction solvent was changed from 1,3,6-trimethylhexahydro-1,3,6-triazocine-2-on to 1,3,6-tri-n-propylhexahydro-1,3,6-triazocine-2-on.

4,4'-Bis(3-aminophenoxy)benzophenone was obtained in the yield of 88.0%.

Reference Example 3

The same procedures as described in Reference Example 1 were carried out except that the reaction solvent 1,3,6-trimethylhexahydro-1,3,6-triazocine-2-on was replaced by 1,3,6-tri-n-butylhexahydro-1,3,6-triazocine-2-on.

4,4'-Bis(3-aminophenoxy)benzophenone was obtained in the yield of 87.5%.

Reference Example 4

The same procedures as described in Reference Example 1 were carried out except that the reaction solvent 1,3,6-trimethylhexahydro-1,3,6-triazocine-2-on was replaced by 1,3-dimethyl-2-imidazolidinone.

4,4'-Bis(3-aminophenoxy)benzophenone was obtained in the yield of 87.0%.

Reference Example 5

The same procedures as described in Reference Example 1 were carried out except that the reaction solvent 1,3,6-trimethylhexahydro-1,3,6-triazocine-2-on was replaced by N-methyl-2-pyrrolidone.

4,4'-Bis(3-aminophenoxy)benzophenone was obtained in the yield of 76.5%.

What is claimed is:

1. 1,3,6- Trialkylhexahydro-1,3,6-triazocine-2-on represented by the formula (1):

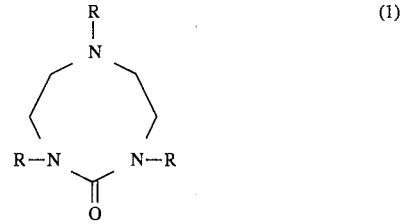

wherein R is a C$_1$~C$_8$ alkyl group.

2. A preparation process of 1,3,6- trialkylhexahydro-1,3,6-triazocine-2-on represented by the formula (1):

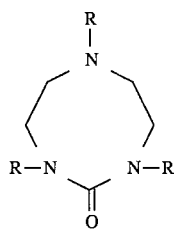
(1)

wherein R is a $C_1 \sim C_8$ alkyl group, comprising reacting N,N',N"-trialkyldiethylenetriamine represented by the formula (2):

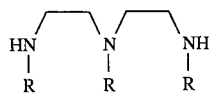
(2)

wherein R is a $C_1 \sim C_8$ alkyl group, with urea, phosgene or carbon dioxide.

3. A preparation process of 1,3,6- trialkylhexahydro-1,3,6-triazocine-2-on represented by the formula (1):

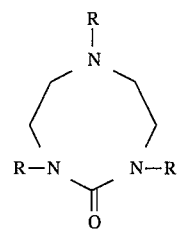
(1)

wherein R is a $C_1 \sim C_8$ alkyl group, comprising reacting N,N',N"-trialkyldiethylenetriamine represented by the formula (2):

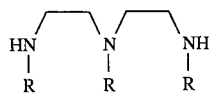
(2)

whrein R is a $C_1 \sim C_8$ alkyl group, with urea.

4. A preparation process of claim 2 wherein the reaction is carried out at 160° C. or less in the first step and at 200° C. or more in the second step.

5. A preparation process of claim 2 wherein the molar ratio of N,N',N"-trialkyldiethylenetriamine to urea is 1.2~1.7.

6. A preparation process of claim 2 wherein the reaction is carried out without solvent.

* * * * *